(12) United States Patent
Subramanian et al.

(10) Patent No.: US 10,814,142 B2
(45) Date of Patent: Oct. 27, 2020

(54) INTRACAVITARY APPLICATOR FOR A MEDICAL PROCEDURE

(71) Applicant: BEST MEDICAL INTERNATIONAL, INC., Springfield, VA (US)

(72) Inventors: Manny R. Subramanian, Frederick, MD (US); Lloyd Michael Cutrer, Huntington Beach, CA (US); Rohit V. Mehta, Clifton, VA (US); A. M. Nisar Syed, Rancho Palos Verde, CA (US); Anil Kumar Sharma, Huntington Beach, CA (US)

(73) Assignee: Best Medical International, Inc., Springfield, VA (US)

( * ) Notice: Subject to any disclaimer, the term of this patent is extended or adjusted under 35 U.S.C. 154(b) by 70 days.

(21) Appl. No.: 16/162,988

(22) Filed: Oct. 17, 2018

(65) Prior Publication Data
US 2019/0117996 A1    Apr. 25, 2019

Related U.S. Application Data

(60) Provisional application No. 62/575,861, filed on Oct. 23, 2017.

(51) Int. Cl.
*A61N 5/10*    (2006.01)

(52) U.S. Cl.
CPC ......... *A61N 5/1016* (2013.01); *A61N 5/1007* (2013.01); *A61N 5/1065* (2013.01)

(58) Field of Classification Search
CPC ...... A61N 5/10; A61N 5/1001; A61N 5/1007; A61N 5/1014; A61N 5/1016; A61N 5/1015
See application file for complete search history.

(56) References Cited

U.S. PATENT DOCUMENTS 9,039,593 B2    5/2015 Lebovic et al.
10,029,119 B2    7/2018 Makel et al.
(Continued)

OTHER PUBLICATIONS

Notification of Transmittal of the International Search Report and the Written Opinion of the International Searching Authority, International Search Report, Written Opinion, and Search History for corresponding PCT Application No. PCT/US2018/056634, dated Dec. 21, 2018, 15 pages.
(Continued)

*Primary Examiner* — Carrie R Dorna (57) ABSTRACT

An intracavitary applicator, such as a vaginal applicator, includes an elongate outer shell selectively housing an elongate cylinder insert, each having an open, proximal end and a closed and curved, distal end. An endcap selectively closes the proximal ends. A central through-bore extends substantially the length of the cylinder insert. Outer guide channels run along the length and around the curved distal end of the cylinder insert to terminate near an opening of the central through-bore. Guide holes and an endcap through-bore on the endcap align and communicate with the guide channels and central through-bore, respectively, when assembled to form pathways for introduction of radioactive sources and/or other instruments. The outer shell has a thinner wall at the distal end than the side to enable the insert to be closer to the target treatment area. An anchor collar can be used to fix positioning of the intracavitary applicator.

25 Claims, 9 Drawing Sheets

(56) References Cited

U.S. PATENT DOCUMENTS

| | | |
|---|---|---|
| 2014/0121445 A1 | 5/2014 | Fontenot et al. |
| 2014/0309478 A1 | 10/2014 | Grigsby |
| 2015/0335913 A1 | 11/2015 | Makel et al. |

OTHER PUBLICATIONS

BrachyNext, "Gynecologic Vaginal Brachytherapy (Mostly Post-Op Endometrial)", Demanes, http://www.aoic.net/elekta/elk1402archive/B101Demanes.pdf, 2014, 15 pages.

BrachyTherapy, "American Brachytherapy Task Group Report: Adjuvant vaginal brachytherapy for early-stage endometrial cancer: A comprehensive review", Harkenrider et al., http://www.brachyjournal.com/article/S1538-4721(16)30049-6/pdf, Abstract, 2017, 2 pages.

Atlas of Pelvic Surgery,"Application of Vaginal Cylinders for Intracavitary Radiation Therapy", Wheeless et al., http://www.atlasofpelvicsurgery.com/10MalignantDisease/4ApplicationofVaginalCylindersforIntracavitaryRadiationTherapy/cha10sec4.html, downloaded 2019, 2 pages.

UCLA Health, "Cervical, Endometrial, Vaginal and Vulvar Cancers Gynecologic Brachytherapy Treatment", http://radonc.ucla.edu/gynecologic-brachytherapy-treatment, https://www.uclahealth.org/radonc/gynecologic-brachytherapy-treatment, downloaded 2019, 8 pages.

Medical Physics, vol. 44, No. 6, 2017 AAPM Annual Meeting Program, SU-E-205-01, "3D Printed Brachytherapy Vaginal Cylinder Applicator with Curved Channel Ends", Gutti et al. 2017, cover page and page 2723, 2 pages.

INTRACAVITARY APPLICATOR FOR A MEDICAL PROCEDURE

CROSS REFERENCE TO RELATED APPLICATION

This application claims priority under 35 U.S.C. § 119 to U.S. Provisional Patent Application No. 62/575,861, filed on Oct. 23, 2017, hereby incorporated herein by reference in its entirety.

FIELD OF THE INVENTION

The present invention relates to medical devices for procedures and treatment, and particularly to an intracavitary applicator for radiation treatment and delivery, such as a vaginal cylinder applicator, that provides maximal radiation exposure and dosage to a target area and increase brachytherapy effectiveness, especially in the cervical region.

BACKGROUND

Cervical cancer was a major cause of death among women of childbearing age in the U.S. till around 1940. With the introduction of Papanicolaou (PAP) smear test that examines possible abnormalities in cervical cells under a microscope, the death rates have declined by about 60%. According to recent data, the incidence rate for cervical cancer was about 8 cases per 100,000 women per year in the U.S. with a mortality rate about 2.4 deaths per 100,000 women per year. To shed some light onto these statistics, an estimated 12,200 women in the U.S. will be diagnosed with cervical cancer in 2010, and an estimated 4,210 will die of this cancer.

Most cervical cancer patients receive radiation therapy and concurrent chemotherapy as part of their treatment. Cisplatin is the most common chemotherapeutic agent used for treatment. Radiation therapy, as part of the main treatment, can be administered by such protocols as radiation alone, surgery followed by radiation, or radiation and chemotherapy combined. Radiation therapy has also been used to treat cancers that have spread to other organs.

There are generally two types of radiation therapy—external beam radiation therapy and intracavitary brachytherapy. In brachytherapy, a radiation source is placed near the cancer inside the body of the patient. For cancers, such as vaginal cancer and cervical cancer in women, the radiation source is introduced in or near the target area via a device, such as a vaginal cylinder, inserted into the vagina. Brachytherapy treatment can be used alone or in combination with external beam radiation therapy. Due to the nature of existing vaginal cylindrical devices, the treatment often can result in incomplete and/or inefficient radiation dosage at the desired cervical area, i.e. most conventional vaginal cylindrical devices are typically unable to provide a sufficient radiation dosage in a single treatment session, often requiting multiple treatment sessions and increased chances of undesirable radiation damage to surrounding healthy tissue.

Typical vaginal cylinders for delivering High Dose Rate (HDR) brachytherapy to vaginal tissue have limited ability for optimized radiation dose delivery due to limitations of the radiation source channels. Current vaginal cylinder applicators generally range in diameters from 2.0 cm to 4.0 cm and a length of approximately 18 cm, for example. The distal end is usually rounded with the proximal end allowing for attachment of source tubes from a HDR unit to allow movement of the radiation source into one or more vaginal cylinder treatment channels. Unfortunately, existing vaginal cylinder applicators can restrict the movement of the radiation source to the side of the vaginal cylinder applicator and can prevent the radiation source from traveling around the distal rounded end of the applicator. Thus, this type of limited placement of the radiation source restricts the ability to extend the radiation dose far towards the distal end of the cylinder where the applicator is generally closest to the potentially malignant tissue in the cervical region.

In light of the above, there is a need for a type of vaginal cylinder applicator that can maximize radiation dosage exposure for more efficient treatment of vaginal, cervical, and other gynecological cancers.

SUMMARY OF THE INVENTION

Embodiments of an intracavitary applicator, such as a vaginal cylinder applicator, for a medical procedure, e.g., radiation or other therapeutic agent delivery and treatment or other therapeutic or diagnostic procedure, includes an elongate outer shell selectively housing an elongate cylinder insert therein. The elongate outer shell and elongate cylinder insert both have an open, proximal end and a closed and curved, distal end. An endcap selectively closes the proximal ends. A central through-bore extends substantially the whole length of the cylinder insert. A plurality of outer guide channels run along the length and around the curved distal end of the cylinder insert to terminate near an exit opening of the central through-bore. A plurality of guide holes and an endcap through-bore on the endcap align and communicate with the guide channels and central through-bore, respectively, when assembled to form pathways for introduction of radioactive sources and/or other instruments. The outer shell has a thinner wall at the distal end than the side to enable the insert to be closer to the target treatment area, thereby increasing efficiency of treatment. One or more anchor collars can be employed to fix positioning of embodiments of the intracavitary applicator.

These and other features of the present invention will become readily apparent upon further review of the following specification and drawings.

DESCRIPTION OF THE DRAWINGS

Unless otherwise indicated, similar reference characters denote corresponding features consistently throughout the attached drawings.

DETAILED DESCRIPTION

Figure 1:
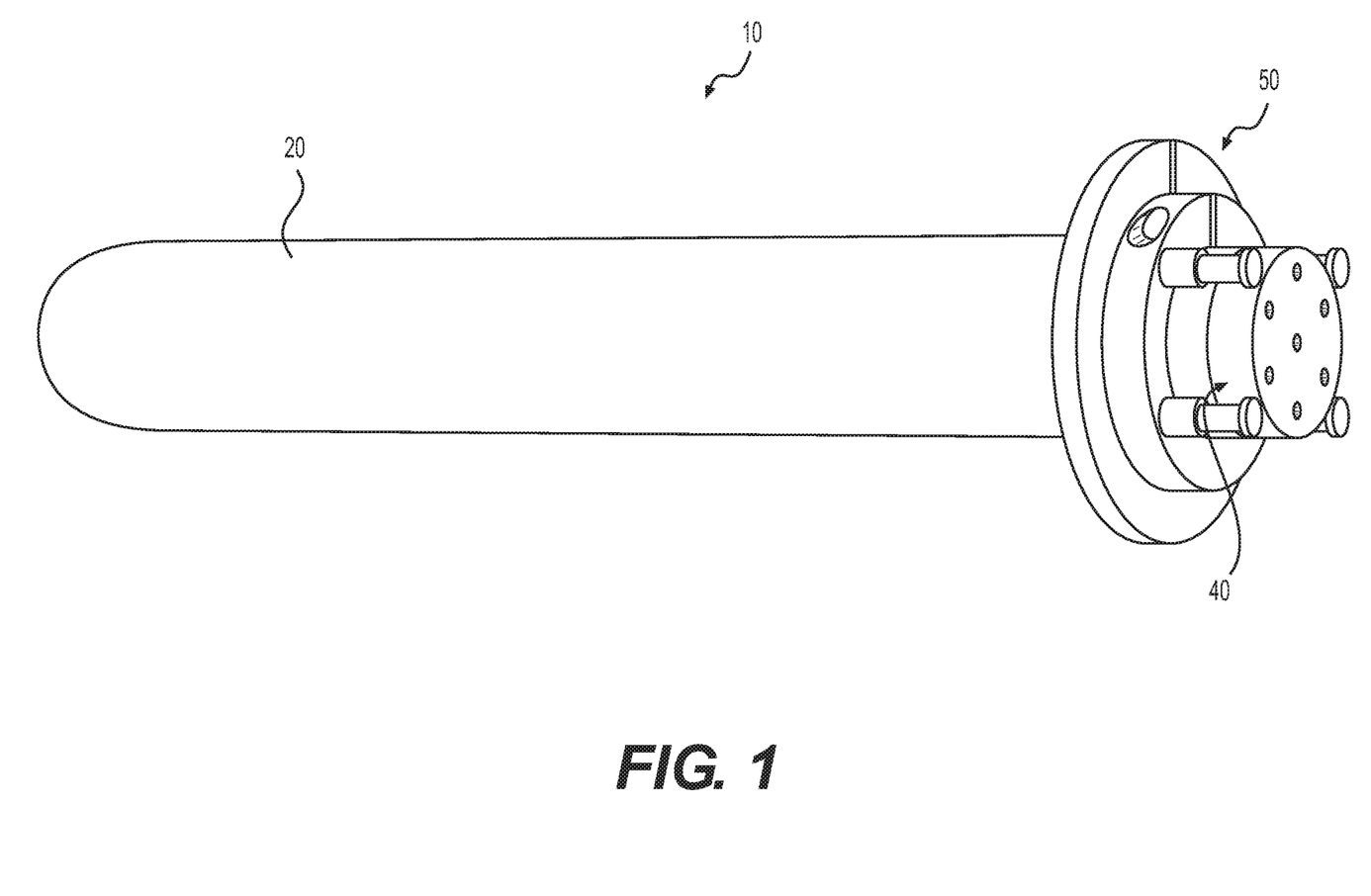
FIG. 1 is an environmental, perspective view of an embodiment of an intracavitary applicator for a medical procedure, such as a vaginal cylinder applicator for radiation delivery, according to the present invention.
Figure 2:
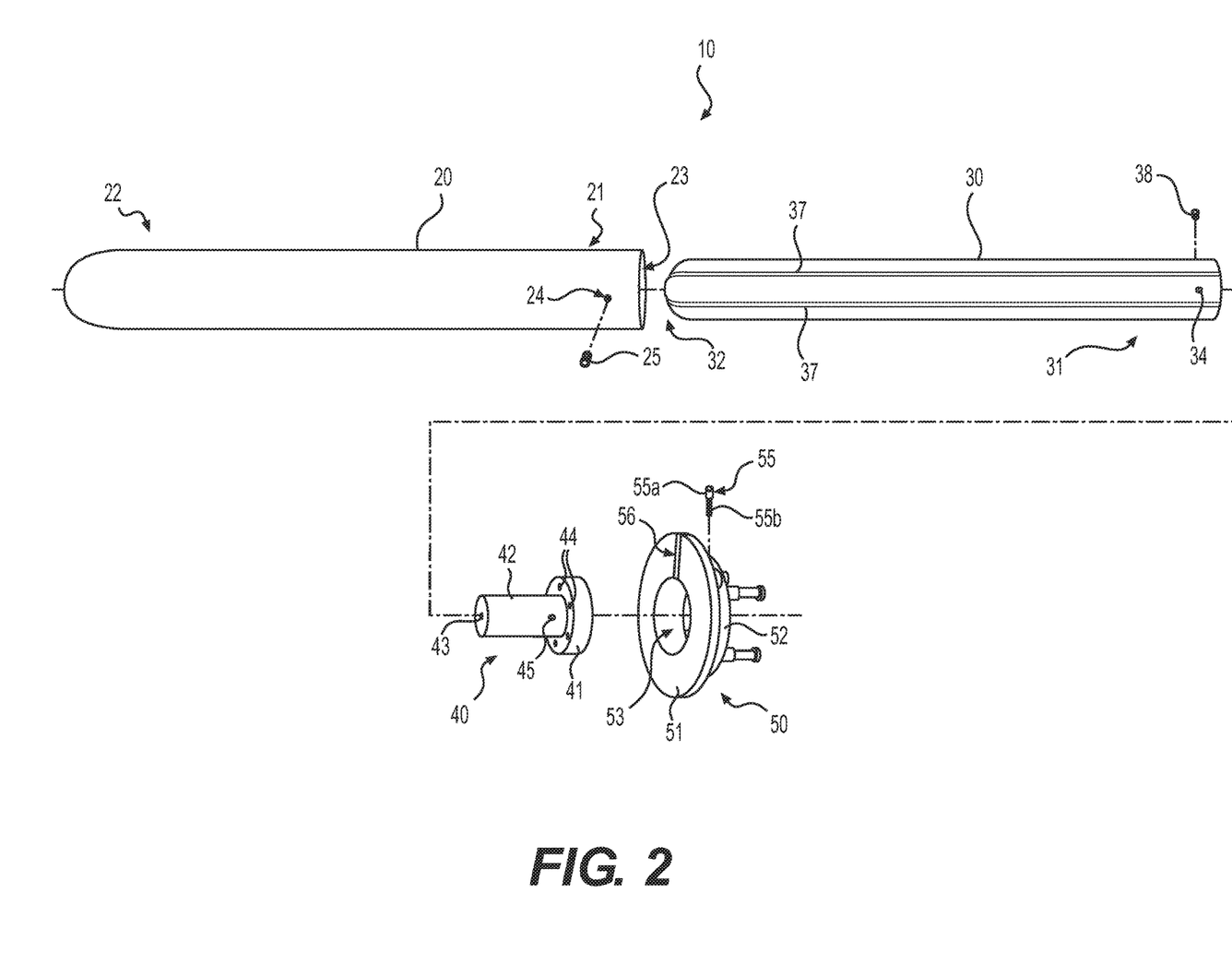
FIG. 2 is an exploded view of the embodiment of an intracavitary applicator shown in FIG. 1, according to the present invention.

Embodiments of an intracavitary applicator for a medical procedure, such as a vaginal cylinder applicator for radiation or other therapeutic agent use or delivery, or such as for instrument use placement in a medical procedure, generally referred to by the reference number 10 in the drawings, delivers maximal radiation dosage to a target area due to structural features that enable the radiation source to reach optimum depth within the intracavitary applicator 10, such as a vaginal cylinder applicator 10, relative to the target area. It is noted that other phrases such as "intracavitary applicator", "vaginal applicator" and "applicator" as used herein refer to embodiments of the intracavitary applicator 10 for a medical procedure, such as a vaginal cylinder applicator 10 for radiation delivery. As best shown in FIGS. 1 and 2, the intracavitary applicator 10 includes an elongate outer shell 20, an elongate cylinder insert 30 selectively coupled inside the outer shell 20, an endcap 40 selectively coupled to the cylinder insert 30, and an anchor collar 50 selectively coupled to a proximal end of the intracavitary applicator 10 to secure the same onto a patient during use.

The outer shell 20 is desirably an elongate, tubular cylinder with an open, base or proximal end 21 and a closed, tip or distal end 22. The distal end 22 is curved to ease insertion of the intracavitary applicator 10 into the patient, such as during the brachytherapy treatment procedure, e.g., such as into the vaginal or cervical area, into other body cavity or surgically created cavity, and the like. The curvature may be rounded as shown, oval, or any other shape that enables ease of insertion. An elongate hollow interior 23 is formed along a substantial length of the outer shell 20 and extends axially from the proximal end 21 to the distal end 22. The hollow interior is dimensioned to slidably house the cylinder insert 30 therein. A threaded setscrew hole 24 is formed near the proximal end 21 and extends into the hollow interior 23. An insert setscrew 25 selectively seats into the setscrew hole 24 to fix the cylinder insert 30 when assembled.

Figure 3A:
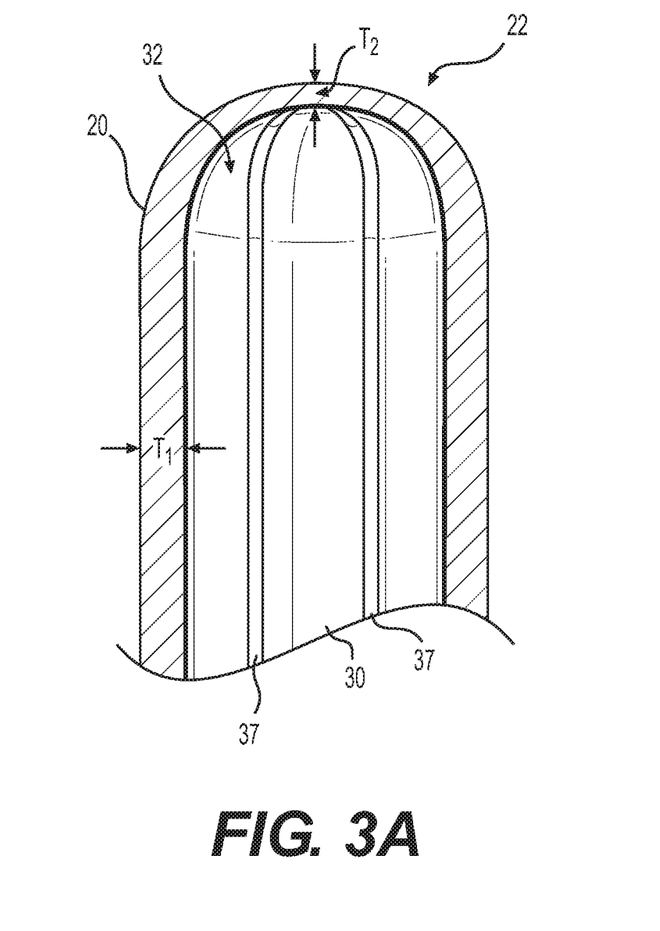
FIG. 3A is a sectional view of an embodiment of an outer shell of the intracavitary applicator shown in FIG. 1 at a distal curved end with an insert disposed therein, according to the present invention.
Figure 3B:
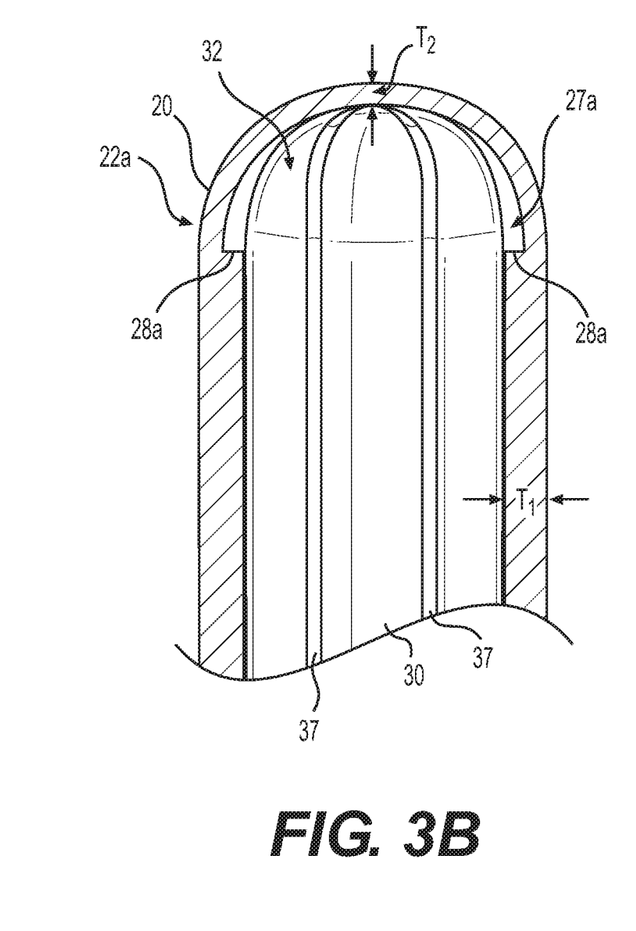
FIG. 3B is a sectional view of another embodiment of an outer shell of the intracavitary applicator shown in FIG. 1 at a distal curved end with an insert disposed therein, according to the present invention.

The outer shell 20 is desirably about 18 cm in length with a diameter of about 2-4 cm, such as when used as a vaginal applicator, for example. These dimensions enable proper placement of the intracavitary applicator 10, e.g., when used as a vaginal applicator, inside a patient and conforms to the anatomy of most patients. However, the dimensions, shape and configuration of the intracavitary applicator 10 and its components can depend on the use and application, and should not be construed in a limiting sense. The tubular, cylindrical shape of the outer shell 20 has a given first wall thickness $T_t$ in a range of about 0.1 mm-0.5 mm along a substantial length thereof, which intrinsically defines an inner and outer diameter of the outer shell 20. As best shown in FIGS. 3A and 3B, the distal end 22, however, has a second wall thickness $T_2$, is desirably equal to or less than half of the first wall thickness $T_1$. However, the first wall thickness $T_1$ and second wall thickness $T_2$ can be of various suitable thicknesses, as can depend on the use or application, and should not be construed in a limiting sense.

The cylinder insert 30 is configured to be selectively mounted inside the outer shell 20 when assembled. As best shown in FIGS. 2, 4, 5A, and 5B, the cylinder insert 30 is also desirably an elongate, generally tubular cylinder with an outer diameter about the same as the inner diameter of the outer shell 20 so as to provide a relatively close fit between the cylinder insert 30 and the outer cylinder 20 when the cylinder insert 30 is coupled therein.

The cylinder insert 30 includes an open, base or proximal end 31 and a closed, tip or distal end 32. The proximal end 31 is provided with an elongate, blind mount recess 33 with a given diameter extending axially a predetermined distance towards the distal end 32. The mount recess 33 facilitates selective mounting of the endcap 40 to close the open, proximal ends of the outer shell 20 and the cylinder insert 30 when assembled. An elongate, central through-bore 36 extends axially from the floor of the mount recess 33 towards the distal end 32 to terminate thereat. The central through-bore 36 defines a center guide channel for threading and passage of a radiation source, probe, catheter, elongate instruments, and the like into the intracavitary applicator 10. The distal end 32 of the cylinder insert 30 is also curved to conform with the interior curvature of the outer shell 20 at the distal end 22 thereof.

One or more elongate, outer guide channels or grooves 37 are formed around the periphery of the cylinder insert 30. The outer guide channels 37 are desirably equidistantly spaced around the outer wall of the cylinder insert 30 and extend from the proximal end 31 towards the distal end 32 to terminate near the opening of the central through-bore 36, i.e., substantially the whole length of the cylinder insert 30 and thereby substantially the length of the intracavitary applicator 10. The central through-bore 36 and the outer guide channels 37 are desirably about 1 mm in width or diameter. It is to be understood that these dimensions can be smaller or larger depending on use or application and should not be construed in a limiting sense. Since the distal end 32 is curved, the outer guide channels 37 also follow that curvature as they approach the exit opening of the through-bore 36. As best seen in FIG. 5B, desirably all the outer guide channels 37 meet near the distal end of the central through-bore 36 and surround the same leaving a generally narrow annular gap between the through-bore 36 and the guide channels 37. Additionally, each outer guide channel 37 is spaced from an adjacent outer guide channel 37 so that they are not contiguous with each other. This arrangement facilitates insured separation of corresponding radiation sources at each guide channel 37 and the through-bore 36 during use of the intracavitary applicator 10 for radiation treatment or therapy, for example.

When assembled with the cylinder insert 30 mounted inside the outer shell 20, the inner wall of the outer shell 20 and the guide channels 37 form generally enclosed guideways for guided threading of typical radiation sources, for example, radiation source tubes from the HDR unit, stranded radioactive sources, and/or other instruments. As best seen in FIG. 3A, the second wall thickness $T_2$ at the distal end 22 of the outer shell 20 enables the radiation sources and/or instruments to be in closer proximity to the target area during use compared to an applicator having uniform wall thickness throughout. Though the closer positioning of the distal end 32 of the cylinder insert 30 can appear relatively small facilitated by the thinner second wall thickness $T_2$ at the distal end 22, the relative distance of the radiation source from the target area is rather sensitive in that it can affect the efficiency of a desired or a required radiation dosage and delivery, i.e., facilitating increased efficiency can increase the potential cure rate of the treatment. It has been found that the efficiency of radiation treatment is greatly increased with the closer proximity of the cylinder insert 30 relative to the outer shell 20 and the radiation sources threaded therein due, in part, to the generally closer proximity of the distal end 22 relative to the target area for treatment.

Referring to FIGS. 3A and 3B, the generally matching curves of the distal ends 22, 32 can enable easier threading of the radiation sources around the curved ends by forcing the radiation sources to follow the curvature. In a desired embodiment shown in FIG. 3A, the wall thickness of the distal end 22 gradually decreases to the second wall thickness $T_2$. In FIG. 3B, another embodiment of an alternative distal end 22a includes a dome-shaped cavity 27a with a diameter greater than the inner diameter of the outer shell 20 forming an annular step 28a therein, the greater diameter being larger by a difference between the first wall thickness $T_1$ and the second wall thickness $T_2$. The dome-shaped cavity 27a defines an inner curved section of the distal end 22a with a generally uniform second wall thickness $T_2$ instead of a gradual decrease in wall thickness from the first wall thickness $T_1$ to the second wall thickness $T_2$ as in FIG. 3A, for example. When assembled, the dome-shaped cavity 27a forms a generally annular gap or space between the cylinder insert 30 and the interior of the distal end 22a. This arrangement including the dome-shaped cavity 27a can be more suitable for less flexible radiation sources that can require more room for bending so as to force conformity with the curved distal end 32.

The endcap 40 includes a disk section or flange 41 and an elongate post section 42 extending axially from one side of the disk section 41. These two sections 41, 42 of the endcap 40 form a general T-shape in cross section. An elongate endcap through-bore 43 extends through both sections 41, 42 and communicates with the central through-bore 36 when coupled to the cylinder insert 30. The endcap through-bore 43 desirably has the same diameter as the central through-bore 36 and can facilitate enabling a user to thread a radiation source or any other instrument from the endcap 40 towards the distal end 32 of the cylinder insert 30, for example. The disk section 41 is desirably flat on both sides and includes one or more axially extending guide holes 44 arranged in a circular pattern around the center axis of the endcap 40. In other words, the guide holes 44 are angularly spaced around the center axis at regular, radial offset positions, but the pattern and spacing of guide holes 44 can also be any of various suitable patterns and spacing, as can depend on the use or application, and should not be construed in a limiting sense. These guide holes 44 can have the same angular spacing and radial position as the outer guide channels 37 so that when connected to the cylinder insert 30, the guide holes 44 align and communicate with corresponding outer guide channels 37. The outer diameter of the disk section 41 is desirably about the same as the outer diameter of the outer shell 20 so that the peripheral surface of the disk section 41 is contiguous with the peripheral surface of the outer shell 20 when assembled to thereby close the proximal ends 21, 31.

The post section 42 is desirably an elongate cylinder that serves as a plug selectively seated inside the mount recess 33, the mount recess 33 acting as a socket. Additionally, the post section 42 enables the endcap 40 to be fixed to the cylinder insert 30 when seated inside the mount recess 33. To facilitate fixed mounting of the endcap 40, the post section 42 desirably can include a setscrew recess 45 disposed on a side thereof configured to selectively receive an endcap setscrew 38 through the cylinder insert 30. The setscrew recess 45 is axially spaced a predetermined distance from the side of the disk section 41.

Figure 4:
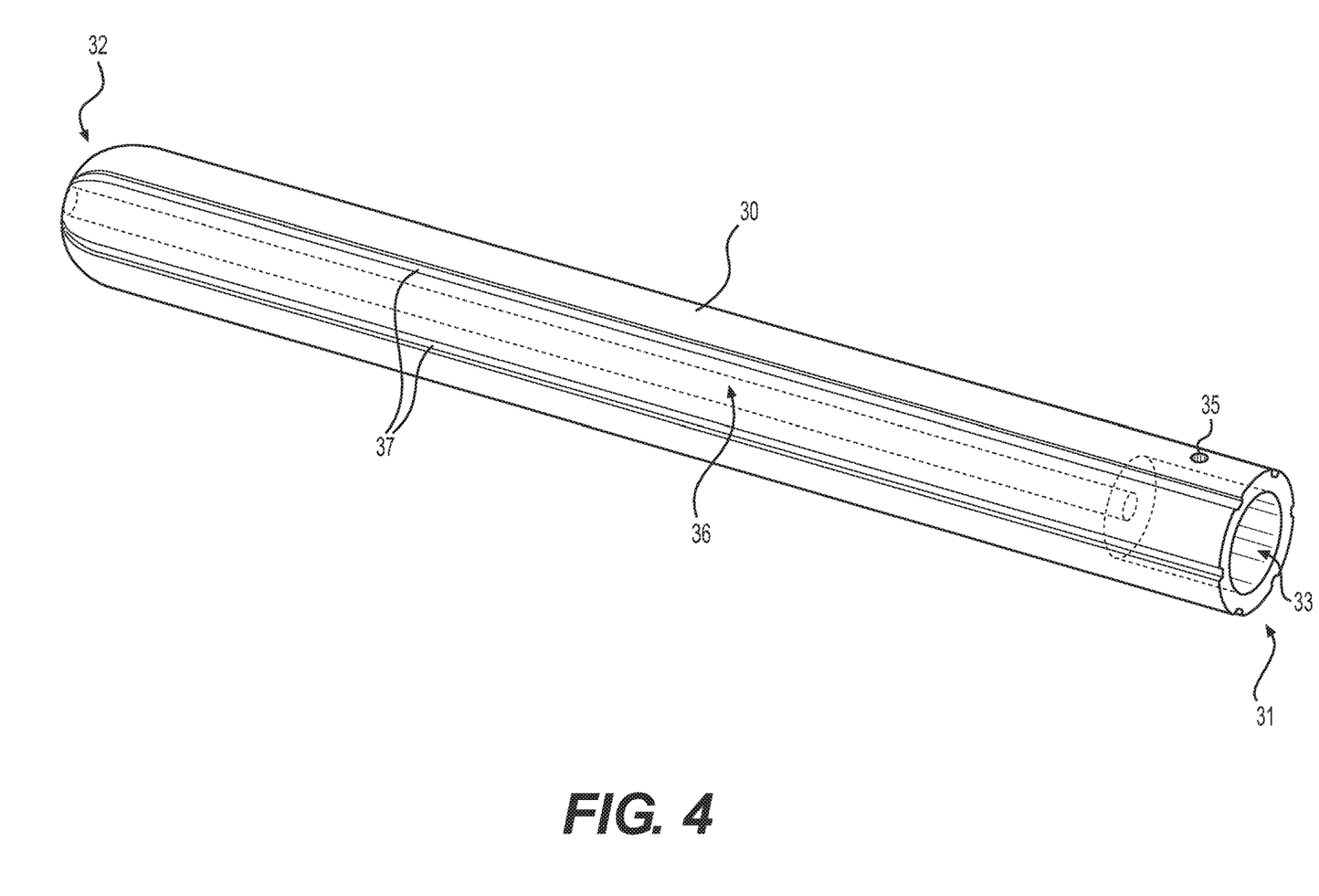
FIG. 4 is a perspective view of an embodiment of an insert for the intracavitary applicator shown in FIG. 1, according to the present invention.
Figure 5A:
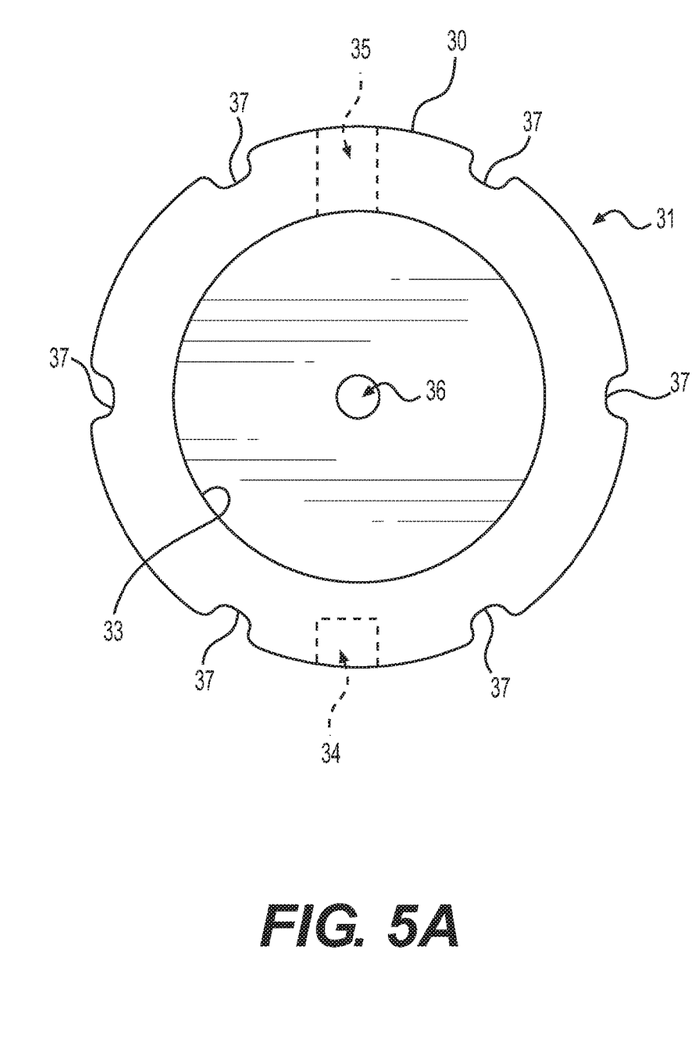
FIG. 5A is a bottom plan view of the insert shown in FIG. 4, according to the present invention.
Figure 5B:
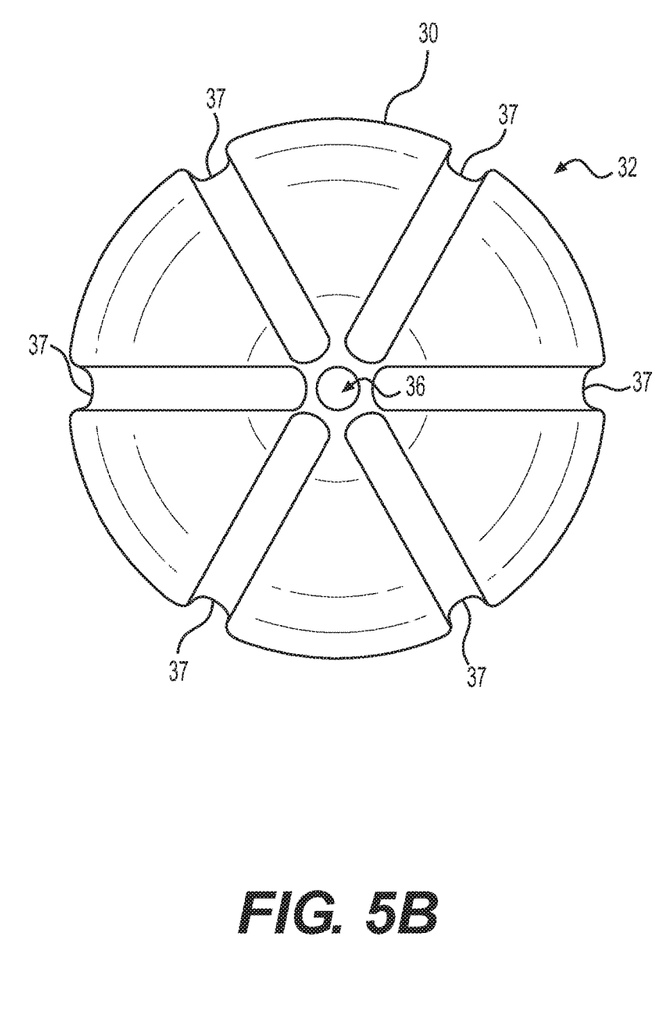
FIG. 5B is a top plan view of the insert shown in FIG. 4, according to the present invention.

As best shown in FIGS. 2, 4, and 5A, the cylinder insert 30 desirably also includes a setscrew recess 34 and a setscrew hole 35 diametrically opposite from the setscrew recess 34. The setscrew hole 35 and/or the setscrew recess 34 can be threaded. The setscrew hole 35 is also axially spaced a predetermined distance from the proximal end 31 so that the setscrew hole 35 aligns and communicates with the setscrew recess 45 on the post section 42 when the endcap 40 is coupled to the cylinder insert 30. In other words, the predetermined axial distance of the setscrew recess 45 is the same as the predetermined axial distance of the setscrew hole 35. An endcap fixing setscrew 38 is threaded through the setscrew hole 35 and seats inside the setscrew recess 45 to fix the endcap 40. This coupled arrangement of the cylinder insert 30 and the endcap 40 forms an insert subassembly for mounting into the outer shell 20, and the insert subassembly is fixed, in turn, by threading the insert setscrew 25 through the setscrew hole 24 on the outer shell 20 to seat inside the setscrew recess 34 on the cylinder insert 30.

The above described components forming a fixed connection of the outer shell 20, the cylinder insert 30, and the endcap 40, which can collectively be referred to as a "cylinder assembly," must be properly or suitably aligned so that the setscrew recesses, setscrew holes, the outer guide channels 37, and the guide holes 44 are in communication with their respective counterparts. If alignment is performed by only using one's eye, it typically can require multiple attempts to manipulate these components into proper or suitable alignment. To aid in the alignment of these components, one or more of the components can be provided with alignment indicia as a visual aid. Such visual aid can include a first alignment notch 26 on the proximal end 21 of the outer shell 20 and a second alignment notch 46 on the periphery of the disk section 41 as exemplarily shown in FIGS. 3C and 6. The alignment notches 26, 46 can be, for example, elongate grooves as shown or protrusions, embedded strips, colored markings, luminescent markers, or any other feature that can serve as a visual aid, as can depend on the use or application, and should not be construed in a limiting sense.

Figure 3C:
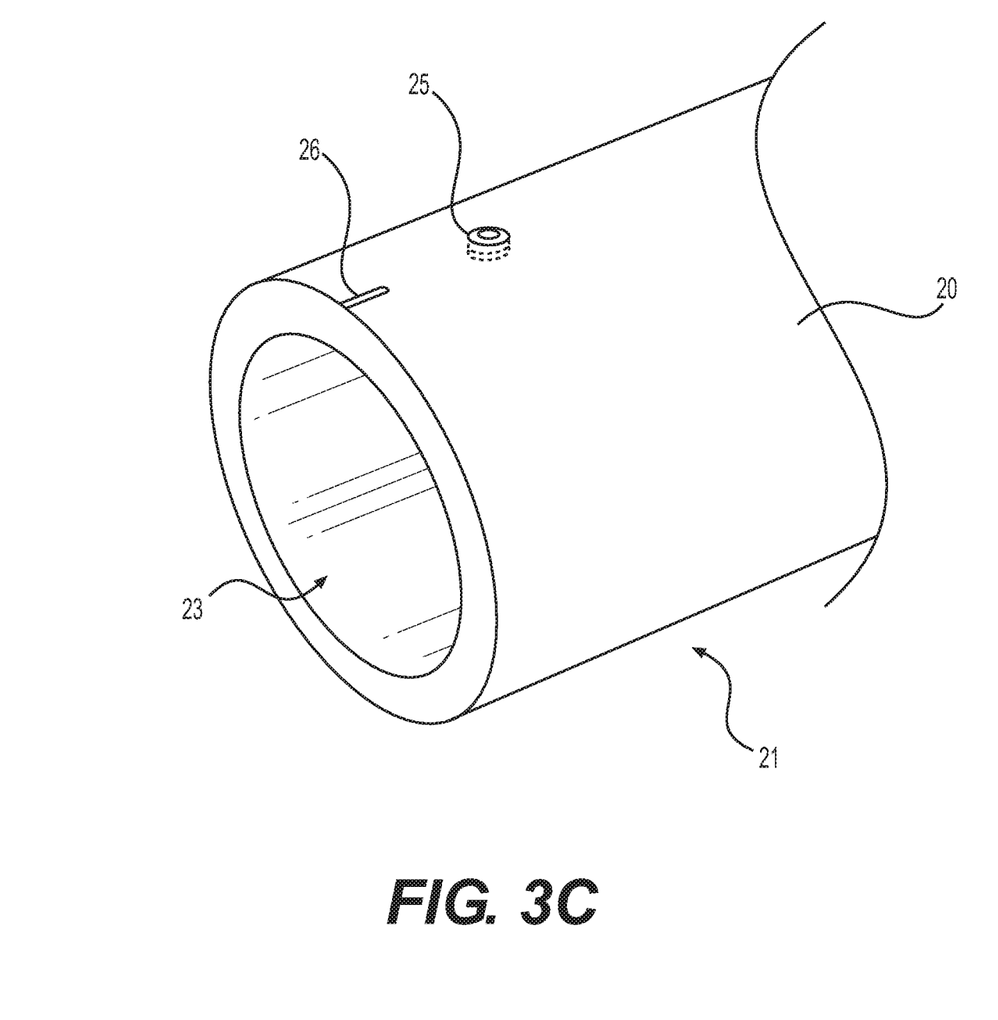
FIG. 3C is a detailed perspective view of a proximal end of an embodiment of the outer shell for the intracavitary applicator shown FIG. 1, according to the present invention.
Figure 6:
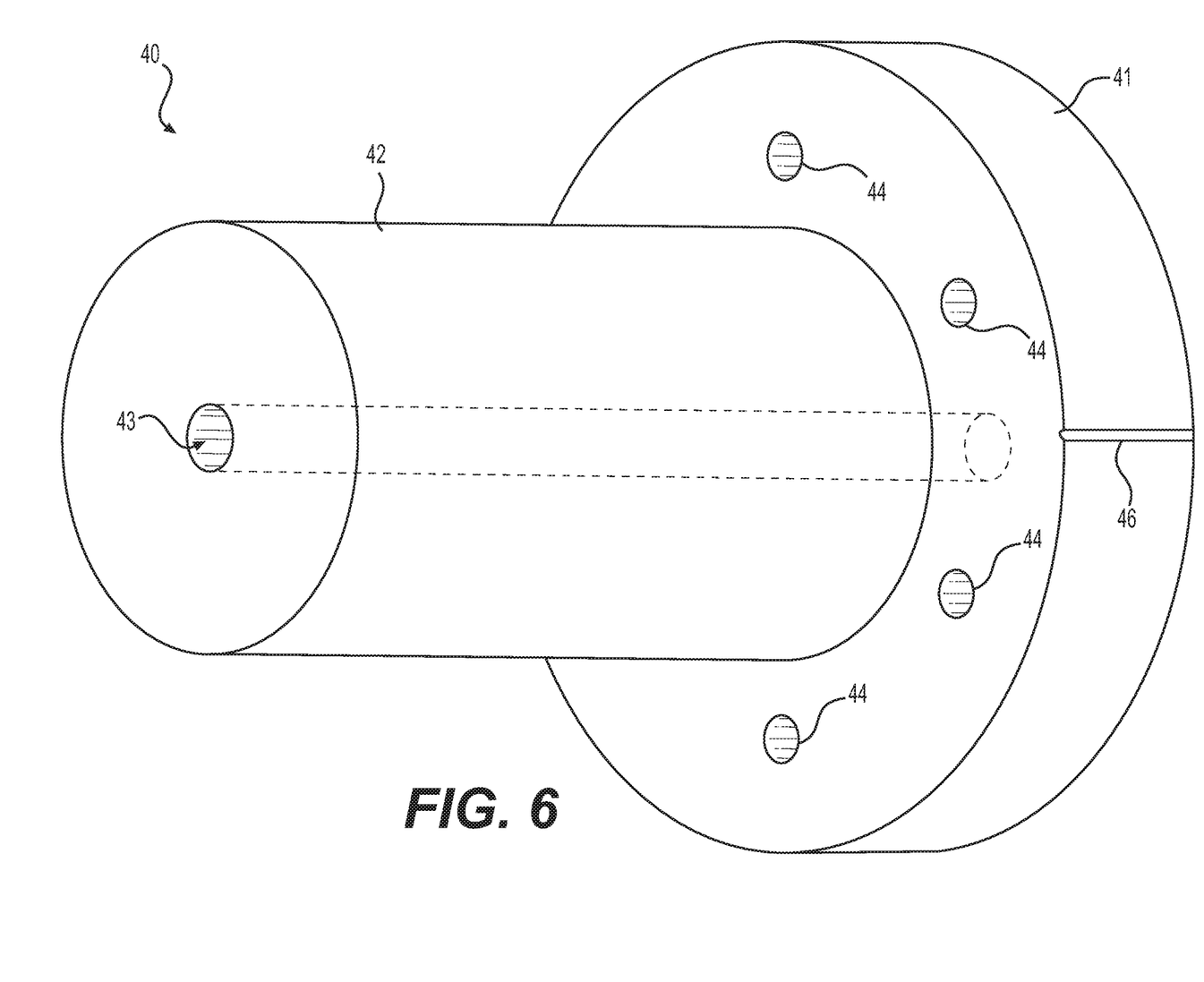
FIG. 6 is a perspective view of an embodiment of an endcap for the intracavitary applicator shown in FIG. 1, according to the present invention.
Figure 7A:
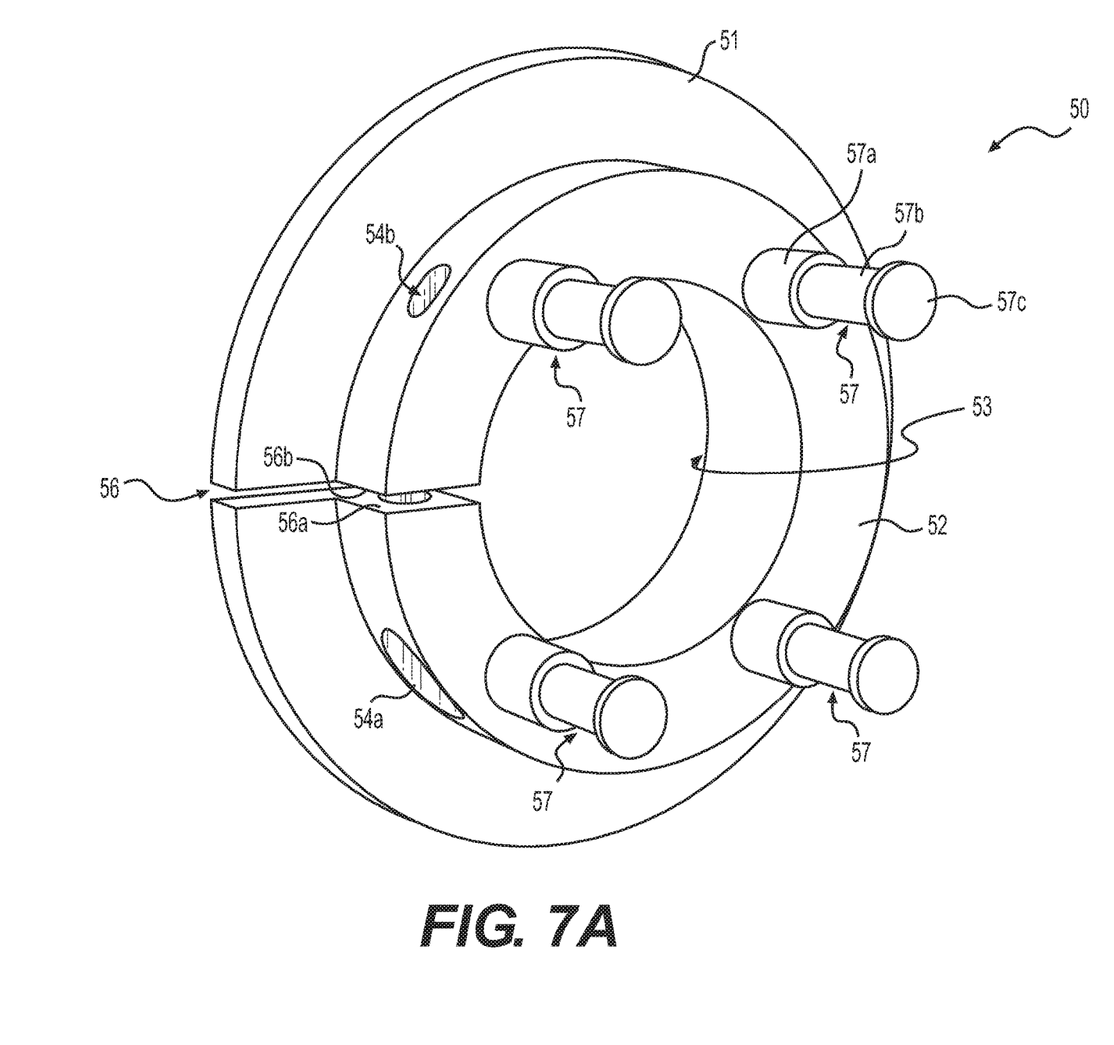
FIG. 7A is a front perspective view of an embodiment of an anchor collar for the intracavitary applicator shown in FIG. 1, according to the present invention.
Figure 7B:
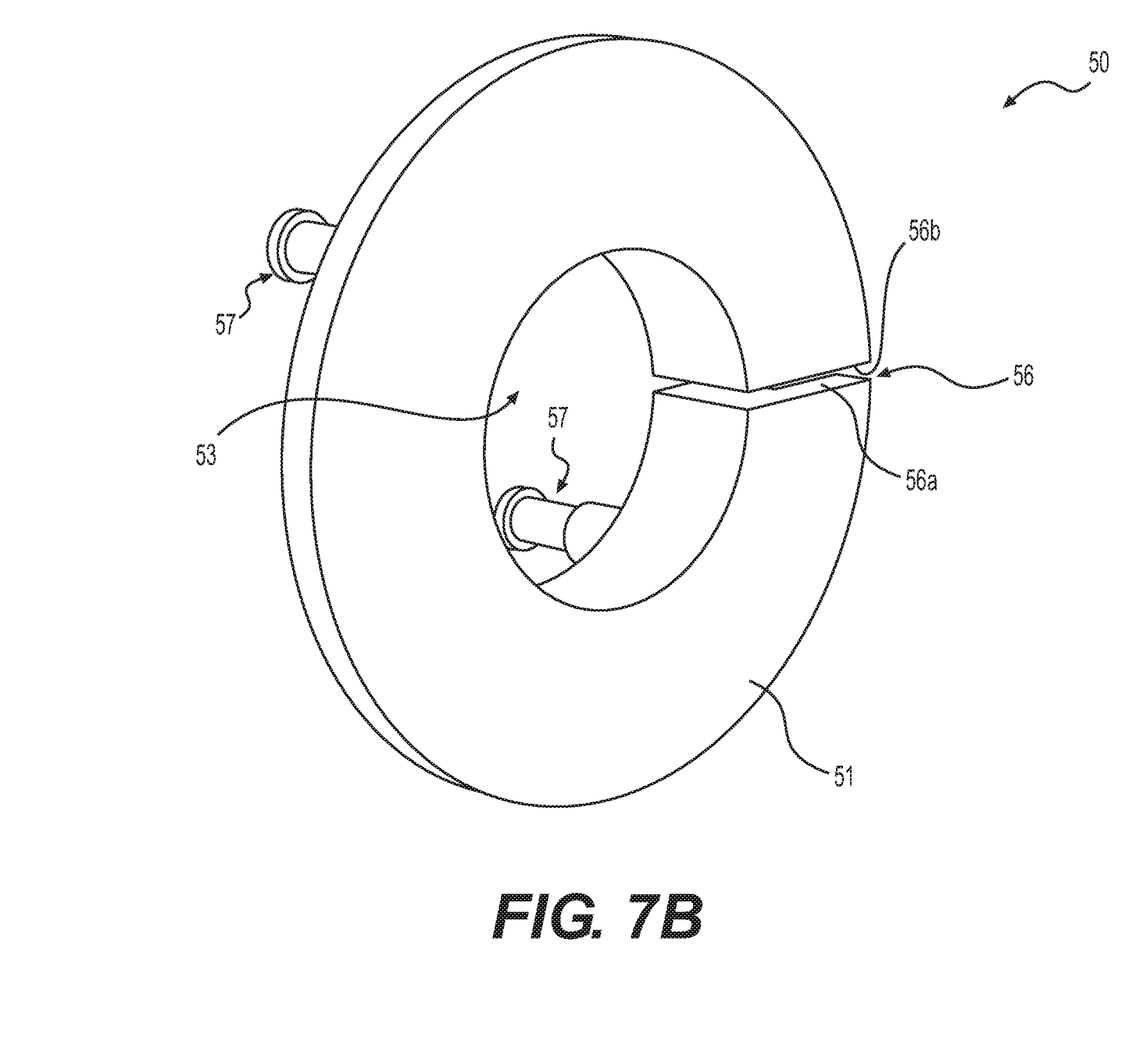
FIG. 7B is a rear perspective view of the anchor collar shown in FIG. 7A, according to the present invention.

As illustrated in FIG. 3C, the first alignment notch 26 is desirably positioned so as to be in line with the setscrew hole 24 that is configured to receive the setscrew. As illustrated in FIG. 6, the second alignment notch 46 is desirably positioned so as to be diametrically opposite, on the disk section 41, from the setscrew recess 45 illustrated in FIG. 2 and angularly halfway between an adjacent pair of guide holes 44. Referring to FIGS. 2, 3C, 4 and 6, this placement of the alignment notches 26, 46 aligns the second alignment notch 46 with the setscrew recess 34 on the cylinder insert 30 in the insert subassembly, which automatically aligns the guide holes 44 with the outer guide channels 37 and the setscrew recess 45 on the post section 42 to the setscrew hole 35 on the cylinder insert 30. When the second alignment notch 46 is aligned with the first alignment notch 26, this arrangement places the setscrew recess 34 on the cylinder insert 30 in communication with the setscrew hole 24 on the outer shell 20.

In another exemplary embodiment of a fixing arrangement in embodiments of the intracavitary applicator 10, the outer shell 20 and the cylinder insert 30 can be provided with a setscrew hole, respectively, in communication with each other. The post section 42 of the endcap 40 can include a setscrew recess in communication with the setscrew hole on the cylinder insert 30 so as to enable a single setscrew to fix all three components together. Also, a further exemplary embodiment of a fixing arrangement in embodiments of the intracavitary applicator 10 can include a threaded connection between the outer shell 20 and the cylinder insert 30 and a threaded connection between the cylinder insert 30 and the endcap 40. In this fixing arrangement, at least the threaded connection between the cylinder insert 30 and the endcap 40 should be suitably precise to align the outer guide channels 37 with the guide holes 44.

The intracavitary applicator 10 such as a vaginal applicator, with the assembled combination of the outer shell 20, cylinder insert 30, and the endcap 40 can be used alone in routine brachytherapy treatments, for example, where the user of the intracavitary applicator 10 threads radiation sources through the guide holes 44 and/or the endcap through-bore 43 and corresponding outer guide channels 37 and central through-bore 36 from the flat outer surface of the endcap 40. Though the drawing figures show six outer guide channels 37 and six guide holes 44, the number, configurations and placement of the outer guide channels 37 and the guide holes 44 can vary, as can depend on the use or application or on user requirements, and should not be construed in a limiting sense. Any changes, however, to the maximum number of guide holes 44 can also require corresponding changes to the outer guide channels 37 on the cylinder insert 30, as well as adjustments to the overall dimension of the components to accommodate the quantity, configuration and dimensions of the guide holes 44 and the outer guide channels 37. Additionally, the guide holes 44 and/or the endcap through-bore 43 can be threaded to enable threaded coupling of connection tubes, such as from an afterloader having one or more radiation sources for radiation delivery to enable automatic or controlled positioning of the radiation source(s) from the afterloader into the intracavitary applicator 10, such as in accordance with commercially available radiation treatment planning software, for example.

In some circumstances, such as when immobility of the device relative to the patient and/or a high degree of accuracy in placing the radioactive source is needed during treatment, the intracavitary applicator 10 can include the anchor collar 50 selectively clamped near the proximal ends 21, 31. As best seen in FIGS. 1, 2, 4, 7A, and 7B, the anchor collar 50 is desirably configured, for example, as a generally stepped and broken/split annular ring with an annular washer head section or flange 51 and a stepped annular hub section 52 extending axially from one planar side of the washer head section 51. A central bore 53 is formed through both sections 51, 52 to slide over and accommodate the assembled cylinder of the outer shell 20 the cylinder insert 30, and the endcap 40. Thus, the central bore 53 typically has a given diameter about the same or greater than the outer diameter of the assembled cylinder, although the diameter the central bore 53 and the outer diameter of the assembled cylinder can vary, as can depend on the use or application, and should not be construed in a limiting sense. The two sections 51, 52 are desirably an integral or unitary component for structural strength. Also, the two sections 51, 52 can be constructed as separate components connected together by fastening means known in the art such as welds, adhesives, fasteners, and the like, as can depend on the use or application, for example.

Further, the washer head section 51 can be generally shaped as a flat washer ring having an outer diameter greater than the outer diameter of the hub section 52. The washer head section 51 serves as a base and a stop abutment that facilitates preventing further insertion of the intracavitary applicator 10 once clamped onto the assembled cylinder. This configuration of the washer head section 51 desirably provides a relatively large area enhancing stability and the abutment function, as described. The washer head section 51 can also act as an adjustable depth limiter limiting the depth of insertion of the intracavitary applicator 10 into the patient during treatment, since the physiology of patients vary greatly from one to another and the anchor collar 50 can desirably assist in accommodating the differences in patient physiology.

The hub section 52 is desirably constructed as a thicker ring compared to the washer head section 51. This thicker hub section 52 contributes to the structural strength of the anchor collar 50. A radial gap 56 extends between both sections 51, 52 to thereby split the anchor collar 50, the radial gap 56 being defined by opposing split ends 56a, 56b. This gap 56 desirably facilitates enabling the anchor collar 50 to easily slide over and be positioned in communicating relation with the proximal ends 21, 31 to a predetermined position along the length of the assembled cylinder of the intracavitary applicator 10.

To enable clamping of the anchor collar 50, the hub section 52 includes a pair of generally opposing setscrew recesses, such as a first setscrew recess 54a and a second setscrew recess 54b, as can extend along a chordal line through the wall of the hub section 52. Each recess 54a, 54b is similar to the mount recess 33 in the cylinder insert 30 to the extent that each recess 54a, 54b includes a small diameter through-bore extending from the floor of the respective recesses 54a, 54b to terminate at the respective split ends 56a, 56b in the radial gap 56 with the through-bores being substantially chordal aligned with each other. A relatively large clamp setscrew 55 threads through the first setscrew recess 54a, passes through the radial gap 56, and threads into the second setscrew recess 54b. Selective tightening of the clamp setscrew 55 forces the split ends 56a, 56b to move toward each other, which constricts the central bore 53 and thereby facilitates clamping the anchor collar 50 onto the assembled cylinder of the intracavitary applicator 10.

The clamp setscrew 55 is typically relatively large compared to the setscrews used to assemble the outer shell 20, the cylinder insert 30, and the endcap 40 into the assembled cylinder of the intracavitary applicator 10. As such, the clamp setscrew 55 has a relatively large head 55a and an elongate threaded bolt 55b of a sufficient length and configuration. The first setscrew recess 54a desirably has an opening greater than the opening on the second setscrew recess 54b to accommodate the relatively large head 55a of the clamp setscrew 55. The smaller opening on the second setscrew recess 54b is about the same diameter as the threaded bolt 55b. The smaller opening on the second setscrew recess 54b can desirably serve as an access point for forming corresponding threads therein and/or maintenance on broken screws, for example.

The intracavitary applicator 10, such as a vaginal applicator, also includes one or more securement posts 57 extending axially from a face of the hub section 52, this face being opposite from the flat face of the washer head section 51. Each securement post 57 includes a cylindrical base 57a extending from the face of the hub section 52, an elongate shaft 57b extending from a distal end of the cylindrical base 57a, and a flat, circular end flange 57c at a distal end of the shaft 57b. The shaft 57b is desirably of smaller diameter than the cylindrical base 57a and of a smaller diameter than the circular end flange 57c so that the cylindrical base 57a and the circular end flange 57c serve as opposing flanges. These securement posts 57 can desirably be used to connect straps or other securing means in a manner known in the art to fix the position of the intracavitary applicator 10 for delivery of a radiation treatment, for example, when used as a vaginal applicator for radiation delivery and treatment.

Thus, it can be seen from the above description that embodiments of the intracavitary applicator 10, such as when used as a vaginal cylinder applicator, can provide a more efficient radiation dosage at the target area by placing the radiation sources, guided by the cylinder insert 30, closer to the malignant tissue during use. Moreover, the intracavitary applicator 10 can also facilitate a relatively high sanitary operation and can be more economical in relation to conventional applicators. In this regard, embodiments of the intracavitary applicator, such as the intracavitary applicator 10, can be desirably utilized in that, in appropriate treatment applications, only the outer shell 20 and/or the anchor collar 50 of the intracavitary applicator 10 typically will be subject to contact with the patient. In such applications, the cylinder insert 30 and the endcap 40 are typically not exposed to patient con act since the insert 30 is encased by the outer shell 20 and the endcap 40 is at the extreme proximal end. Therefore, only the outer shell 20 and/or the anchor collar 50 require cleaning and sterilization prior to use on another patient. In regards to the latter, the intracavitary applicator 10 can be reusable, but can also be made to be disposable, as well. As described herein, in some instances and uses, desirably only some of the components, such as the outer shell 20 and the anchor collar 50, can require more frequent cleaning, and these can be easily replaced at minimal cost.

Embodiments of the intracavitary applicator 10 can desirably be constructed from various suitable materials, such as durable, bio-compatible, medical grade polymeric materials so that the various components can withstand the rigors of repeated cleaning and sterilization processes. For example, the intracavitary applicator 10 can be constructed from other suitable bio-compatible, medical grade materials, such as plastics, wood, metal, composites, and combinations thereof. However, materials that can possibly hinder imaging instruments or retard radiation delivery, such as ferric metals, lead, and the like, are typically less desired, for certain radiation treatment procedures. Some examples of suitable polymeric materials can include polyurethane, polyethylene, polymethyl methacrylate (PMMA), polycarbonate, styrenic block copolymers, polybutylene terephthalate (PBT), Teflon, Nylon, and polyvinyl chloride (PVC).

It is to be understood that embodiments of the intracavitary applicator of the present invention can encompass a variety of constructions, configurations, materials and uses, as can depend on the use or application, and should not be construed in a limiting sense. For example, though the guide holes 44 and the corresponding outer guide channels 37 have been shown and described as being arranged in a regular pattern, such as the exemplary pattern illustrated in the Figures, this pattern can also be irregular or a combination of both depending on a specific arrangement desired or required by the user, as can depend on the use or application, and should not be construed in a limiting sense. Generally, as long as the patterned arrangement enables the guide holes 44 and outer guide channels 37 to suitably align and communicate with each other, such as for receiving the radiation source or other instruments, such suitable arrangement can be acceptable and typically will not affect the relatively close proximity reach afforded by the intracavitary applicator 10 for the radiation source(s) or instruments) during a procedure, such as a radiation treatment.

Further, the intracavitary applicator 10 can also be presented in a variety of colors and/or indicia, such as organizational names, color codes, and the like. Moreover, as described, the intracavitary applicator 10 can be constructed in different suitable geometric, cross-sectional shapes and configurations, such as oval, polygonal, and the like, as long as these various shapes do not significantly negatively impact the insertion process nor the comfort or treatment of the patient for a medical procedure.

As also evident from the foregoing, embodiments of the intracavitary applicator, in addition to use in human treatments, can have applicability and use in veterinary treatments, such as, for example, in the treatment of animals, mammals, fish, birds and reptiles, and in this regard, should not be construed in a limiting sense.

It is to be understood that the present invention is not limited to the embodiments described above, but encompasses any and all embodiments within the scope of the following claims.

We claim:

1. An intracavitary applicator for a medical procedure, comprising:

an elongate, unitary hollow outer shell having a given length and an outer diameter, an open proximal end, and a closed and curved distal end, the curved distal end having a curved closed tip, the outer shell having an inner wall, a first wall thickness on a side, and a second wall thickness at the distal end, the second wall thickness defined by a distance between the inner wall and an outer surface of the curved closed tip, the second wall thickness being smaller than the first wall thickness;

an elongate insert selectively coupled to the outer shell from the open proximal end of the outer shell, the elongate insert having a given length, an open proximal end, a curved distal end, an elongate central through-bore extending substantially the whole length of the elongate insert with one end terminating at the distal end, and at least one outer guide channel formed on an outer surface of the elongate insert, the at least one outer guide channel extending from the proximal end to the distal end of the elongate insert, the at least one outer guide channel and the inner wall of the outer shell defining at least one enclosed pathway; and an endcap selectively coupled to the proximal end of the elongate insert to close the proximal ends of the elongate insert and the outer shell when assembled, the endcap having an axially extending endcap through-bore and at least one angularly spaced guide hole, the endcap through-bore and the at least one guide hole communicating and aligned with the central through-bore and the at least one outer guide channel of the elongate insert, respectively, to facilitate selective positioning of at least one instrument or therapeutic agent for the medical procedure from outside the endcap towards the distal end of the elongate insert, wherein the smaller second wall thickness facilitates closer placement of the at least one instrument or therapeutic agent carried within the at least one outer guide channel or the central through-bore to a target area for the medical procedure.

2. The intracavitary applicator for a medical procedure according to claim 1, wherein said outer shell comprises a setscrew hole formed adjacent said proximal end of said outer shell and a setscrew selectively coupled to said setscrew hole to fix said elongate insert when assembled.

3. The intracavitary applicator for a medical procedure according to claim 1, wherein said elongate insert comprises:
   a setscrew recess formed adjacent said proximal end of said elongate insert, said setscrew recess adapted to receive a setscrew from said outer shell to fix said elongate insert within said outer shell when assembled;
   a setscrew hole formed adjacent said proximal end of said elongate insert and diametrically opposite from said setscrew recess;
   a mount recess formed on said proximal end of said elongate insert axially extending to a given depth, said mount recess adapted to selectively receive said endcap therein, said opposite end of said central through-bore of said elongate insert terminating at a floor of said mount recess; and
   an endcap setscrew selectively coupled to said setscrew hole to fix said endcap when assembled.

4. The intracavitary applicator for a medical procedure according to claim 1, wherein said endcap comprises:
   a disk section having an outer diameter about the same diameter as said outer diameter of said outer shell, said disk section having said at least one guide hole formed thereon;
   an elongate post section extending axially from one side of said disk section, said post section selectively coupled to said proximal end of said elongate insert to close said proximal end, said endcap through-bore extending through both said disk section and said post section with one end communicating with said central through-bore in said elongate insert and the opposite end terminating on an opposite side of said disk section; and
   a setscrew recess formed on said post section, said setscrew recess adapted to receive an endcap setscrew from said elongate insert to fix said endcap when assembled.

5. The intracavitary applicator for a medical procedure according to claim 1, further comprising:
   an alignment means for assisting in aligning said outer shell, said cylinder insert, and said endcap.

6. The intracavitary applicator for a medical procedure according to claim 5, wherein said alignment means comprises a first alignment notch disposed on said proximal end of said outer shell and a second alignment notch formed on a periphery of said endcap.

7. The intracavitary applicator for a medical procedure according to claim 1, further comprising:
   an anchor collar selectively coupled to said outer shell, said anchor collar configured to maintain fixed positioning of said intracavitary applicator on a patient during treatment.

8. The intracavitary applicator for a medical procedure according to claim 1, wherein said medical procedure comprises a brachytherapy treatment.

9. The intracavitary applicator for a medical procedure according to claim 1, wherein said medical procedure comprises a radiation delivery procedure.

10. The intracavitary applicator for a medical procedure according to claim 1, wherein said intracavitary applicator is a vaginal applicator.

11. The intracavitary applicator for a medical procedure according to claim 10, wherein said medical procedure comprises a radiation delivery procedure.

12. A vaginal cylinder applicator for brachytherapy treatment, comprising:
   an elongate, unitary hollow outer shell having a given length and an outer diameter, an open proximal end, and a closed and curved distal end, the curved distal end having a curved closed tip, the outer shell having an inner wall, a first wall thickness on a side, and a second wall thickness at the distal end, the second wall thickness defined by a distance between the inner wall and an outer surface of the curved closed tip, the second wall thickness being smaller than the first wall thickness;
   an elongate cylinder insert selectively coupled to the outer shell from the open proximal end of the outer shell, the cylinder insert having a given length, an open proximal end, a curved distal end, an elongate central through-bore extending substantially the whole length of the cylinder insert with one end terminating at the distal end, and at least one outer guide channel formed on an outer surface of the cylinder insert, the at least one outer guide channel extending from the proximal end to the distal end of the cylinder insert, the at least one outer guide channel and the inner wall of the outer shell defining at least one enclosed pathway; and
   an endcap selectively coupled to the proximal end of the cylinder insert to close the proximal ends of the cylinder insert and the outer shell when assembled, the endcap having an axially extending endcap through-bore and at least one angularly spaced guide hole, the endcap through-bore and the at least one guide hole communicating and aligned with the central through-bore and the at least one outer guide channel of the cylinder insert, respectively, to facilitate selective threading of an elongate instrument or a radiation source through the central through-bore or the at least one enclosed pathway from outside the endcap towards the distal end of the cylinder insert,
   wherein the smaller second wall thickness permits closer placement of the elongate instrument or the radiation source carried within the at least one outer guide channel or the central through-bore to a target area for more effective treatment.

13. The vaginal cylinder applicator for brachytherapy treatment according to claim 12, wherein said outer shell comprises a setscrew hole formed adjacent said proximal end of said outer shell and a setscrew selectively coupled to said setscrew hole to fix said cylinder insert when assembled.

14. The vaginal cylinder applicator for brachytherapy treatment according to claim 12, wherein said cylinder insert comprises:
   a setscrew recess formed adjacent said proximal end of said cylinder insert, said setscrew recess adapted to receive a setscrew from said outer shell to fix said cylinder insert within said outer shell when assembled;
   a setscrew hole formed adjacent said proximal end of said cylinder insert and diametrically opposite from said setscrew recess;
   a mount recess formed on said proximal end of said cylinder insert axially extending to a given depth, said mount recess adapted to selectively receive said endcap therein, an opposite end of said central through-bore of said cylinder insert terminating at a floor of said mount recess; and
an endcap setscrew selectively coupled to said setscrew hole to fix said endcap when assembled.

15. The vaginal cylinder applicator for brachytherapy treatment according to claim 12, wherein said endcap comprises:
a disk section having an outer diameter about the same diameter as said outer diameter of said outer shell, said disk section having said at least one guide hole formed thereon;
an elongate post section extending axially from one side of said disk section, said post section selectively coupled to said proximal end of said cylinder insert to close said proximal end, said endcap through-bore extending through both said disk section and said post section with one end communicating with said central through-bore in said cylinder insert and the opposite end terminating on an opposite side of said disk section; and
a setscrew recess formed on said post section, said setscrew recess adapted to receive an endcap setscrew from said cylinder insert to fix said endcap when assembled.

16. The vaginal cylinder applicator for brachytherapy treatment according to claim 12, further comprising:
an alignment means for assisting in aligning said outer shell, said cylinder insert, and said endcap.

17. The vaginal cylinder applicator for brachytherapy treatment according to claim 16, wherein said alignment means comprises a first alignment notch disposed on said proximal end of said outer shell and a second alignment notch formed on a periphery of said endcap.

18. The vaginal cylinder applicator for brachytherapy treatment according to claim 12, further comprising:
an anchor collar selectively coupled to said outer shell, said anchor collar configured to maintain fixed positioning of said vaginal cylinder applicator on a patient during treatment.

19. An intracavitary applicator for a medical procedure, comprising:
an outer shell having an open proximal end and a closed distal end, the closed distal end having a closed tip, the outer shell having an inner wall, a first wall thickness on a side and a second wall thickness at the distal end, the second wall thickness defined by a distance between the inner wall and an outer surface of the closed tip;
an elongate insert selectively positioned within the outer shell from the open proximal end of the outer shell, the elongate insert having an open proximal end, a distal end, an elongate central through-bore extending in the elongate insert, and at least one outer guide channel formed on the elongate insert, the at least one outer guide channel extending from the proximal end of the elongate insert, the at least one outer guide channel defining at least one pathway; and
an endcap selectively coupled to the proximal end of the elongate insert, the endcap having an axially extending endcap through-bore and at least one guide hole, the endcap through-bore and the at least one guide hole communicating and aligned with the central through-bore and the at least one outer guide channel of the elongate insert, respectively, to facilitate selective positioning of an instrument or a therapeutic agent for the medical procedure through the central through-bore or the at least one pathway from outside the endcap towards the distal end of the elongate insert,
wherein the second wall thickness at the distal end of the outer shell facilitates closer placement of the instrument or the therapeutic agent carried within the central through-bore or the at least one outer guide channel to a target area for the medical procedure.

20. The intracavitary applicator for a medical procedure according to claim 19, wherein the medical procedure comprises a brachytherapy treatment.

21. The intracavitary applicator for a medical procedure according to claim 19, wherein the medical procedure comprises a radiation delivery procedure.

22. The intracavitary applicator for a medical procedure according to claim 19, wherein the intracavitary applicator is a vaginal applicator.

23. The intracavitary applicator for a medical procedure according to claim 22, wherein the medical procedure comprises a radiation delivery procedure.

24. An intracavitary applicator for a medical procedure, comprising:
an elongate hollow outer shell having a given length and an outer diameter, an open proximal end, and a closed and curved distal end, the outer shell having a first wall thickness on a side and a second wall thickness at the distal end, the second wall thickness being smaller than the first wall thickness;
an elongate insert selectively coupled to the outer shell from the open proximal end of the outer shell, the elongate insert having a given length, an open proximal end, a curved distal end, an elongate central through-bore extending substantially the whole length of the elongate insert with one end terminating at the distal end, and at least one outer guide channel formed on an outer surface of the elongate insert, the at least one outer guide channel extending from the proximal end to the distal end of the elongate insert, the at least one outer guide channel and an inner wall of the outer shell defining at least one enclosed pathway, the outer shell having a setscrew hole formed adjacent the proximal end of the outer shell and a setscrew selectively coupled to the setscrew hole to fix the elongate insert when assembled; and
an endcap selectively coupled to the proximal end of the elongate insert to close the proximal ends of the elongate insert and the outer shell when assembled, the endcap having an axially extending endcap through-bore and at least one angularly spaced guide hole, the endcap through-bore and the at least one guide hole communicating and aligned with the central through-bore and the at least one outer guide channel of the elongate insert, respectively, to facilitate selective positioning of at least one instrument or therapeutic agent for the medical procedure from outside the endcap towards the distal end of the elongate insert,
wherein the smaller second wall thickness facilitates closer placement of the at least one instrument or therapeutic agent carried within the at least one outer guide channel or the central through-bore to a target area for the medical procedure.

25. A vaginal cylinder applicator for brachytherapy treatment, comprising:
an elongate hollow outer shell having a given length and outer diameter, an open proximal end, and a closed and curved distal end, the outer shell having a first wall thickness on a side and a second wall thickness at the distal end, the second wall thickness being smaller than the first wall thickness;

an elongate cylinder insert selectively coupled to the outer shell from the open proximal end of the outer shell, the cylinder insert having a given length, an open proximal end, a curved distal end, an elongate central through-bore extending substantially the whole length of the cylinder insert with one end terminating at the distal end, and at least one outer guide channel formed on an outer surface of the cylinder insert, the at least one outer guide channel extending from the proximal end to the distal end of the cylinder insert, the at least one outer guide channel and an inner wall of the outer shell defining at least one enclosed pathway, the outer shell having a setscrew hole formed adjacent the proximal end of the outer shell and a setscrew selectively coupled to the setscrew hole to fix the cylinder insert when assembled; and an endcap selectively coupled to the proximal end of the cylinder insert to close the proximal ends of the cylinder insert and the outer shell when assembled, the endcap having an axially extending endcap through-bore and at least one angularly spaced guide hole, the endcap through-bore and the at least one guide hole communicating and aligned with the central through-bore and the at least one outer guide channel of the cylinder insert, respectively, to facilitate selective threading of an elongate instrument or a radiation source through the central through-bore or the at least one enclosed pathway from outside the endcap towards the distal end of the cylinder insert, wherein the smaller second wall thickness permits closer placement of the elongate instrument or the radiation source carried within the at least one outer guide channel or the central through-bore to a target area for more effective treatment.

* * * * *